(12) United States Patent
Park et al.

(10) Patent No.: US 9,895,067 B2
(45) Date of Patent: Feb. 20, 2018

(54) APPARATUS AND METHOD FOR SIMULTANEOUSLY DETECTING SURFACE PRESSURE AND BLOOD VOLUME

(71) Applicant: SAMSUNG ELECTRONICS CO., LTD., Suwon-si (KR)

(72) Inventors: Sangyun Park, Hwaseong-si (KR); Jaemin Kang, Seoul (KR); Yongjoo Kwon, Yongin-si (KR); Sunkwon Kim, Suwon-si (KR); Younho Kim, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/720,267

(22) Filed: Sep. 29, 2017

(65) Prior Publication Data
US 2018/0020934 A1 Jan. 25, 2018

Related U.S. Application Data

(62) Division of application No. 14/926,073, filed on Oct. 29, 2015, now abandoned.

(30) Foreign Application Priority Data

Jan. 12, 2015 (KR) .................. 10-2015-0004448

(51) Int. Cl.
*A61B 5/021* (2006.01)
*A61B 5/0295* (2006.01)
(Continued)

(52) U.S. Cl.
CPC ........ *A61B 5/02141* (2013.01); *A61B 5/0261* (2013.01); *A61B 5/0295* (2013.01);
(Continued)

(58) Field of Classification Search
CPC .............. A61B 5/02141; A61B 5/6843; A61B 5/02416; A61B 5/0261; A61B 5/0295;
(Continued)

(56) References Cited

U.S. PATENT DOCUMENTS

| 8,451,449 B2 | 5/2013 | Holland |
| 8,628,476 B2 | 1/2014 | Utsuno et al. |

(Continued)

FOREIGN PATENT DOCUMENTS

| JP | 3443688 B2 | 6/2003 |
| JP | 2012-161507 A | 8/2012 |
| KR | 10-2014-0031589 A | 3/2014 |

OTHER PUBLICATIONS

Notice of Allowance issued in parent U.S. Appl. No. 14/926,073 dated Jul. 10, 2017.

*Primary Examiner* — Mark W Bockelman
(74) *Attorney, Agent, or Firm* — Sughrue Mion, PLLC (57) ABSTRACT

An apparatus for simultaneously detecting surface pressure and blood volume of an object and a method of detecting the same are provided. The apparatus includes a printed circuit board (PCB); a light emitter disposed on the PCB which emits light of a first wavelength and light of a second wavelength; a first light receiver which detects light of the first wavelength and a second light receiver which detects light of the second wavelength; a transparent elastic body on the PCB which covers the light emitter, the first light receiver, and the second light receiver; and a dichroic coating formed on the transparent elastic body. The dichroic coating reflects light of the first wavelength and transmits light of the second wavelength.

13 Claims, 4 Drawing Sheets

(51) Int. Cl.
*A61B 5/00* (2006.01)
*A61B 5/026* (2006.01)
*A61B 5/024* (2006.01)

(52) U.S. Cl.
CPC ........ *A61B 5/02416* (2013.01); *A61B 5/6843* (2013.01); *A61B 5/6816* (2013.01); *A61B 5/6826* (2013.01); *A61B 2562/166* (2013.01)

(58) Field of Classification Search
CPC ................ A61B 5/6826; A61B 5/6816; A61B 2562/166
See application file for complete search history.

(56) References Cited

U.S. PATENT DOCUMENTS

| | | |
|---|---|---|
| 2012/0271121 A1 | 10/2012 | Della Torre et al. |
| 2016/0206221 A1 | 7/2016 | Kim et al. |
| 2016/0206251 A1 | 7/2016 | Kwon et al. |
| 2017/0007138 A1 * | 1/2017 | Kim .................. A61B 5/02427 |

* cited by examiner

FIG. 6

APPARATUS AND METHOD FOR SIMULTANEOUSLY DETECTING SURFACE PRESSURE AND BLOOD VOLUME

RELATED APPLICATION

This is a divisional of U.S. application Ser. No. 14/926,073 filed on Oct. 29, 2015, which claims priority from Korean Patent Application No. 10-2015-0004448, filed on Jan. 12, 2015, in the Korean Intellectual Property Office, the disclosures of which are incorporated herein in their entirety by reference.

BACKGROUND

1. Field

Apparatuses and methods consistent with exemplary embodiments relate to an apparatus for simultaneously detecting a surface pressure and a blood volume of an object and a method of detecting the same.

2. Description of the Related Art

In order to detect various characteristic of a cardiovascular system, a patient's blood flow may be detected through the surface of the skin. Methods of detecting the blood flow may be largely divided into two types of methods: a method of detecting blood pressure at the surface of the skin by using a pressure sensor, and a method of detecting a change in blood flow under the surface of the skin by using light.

In the case of detecting blood pressure at the surface of the skin, by analyzing the shape of a pressure profile of the skin surface, the elasticity of a blood vessel can be calculated, and thus, the age of the blood vessel or the health of the patient's cardiovascular system may be determined.

In the case of detecting a change in blood flow using light, a ratio of oxyhemoglobin to deoxyhemoglobin is estimated by using light having at least two different wavelengths, and thus, a degree of oxygen saturation may be estimated.

The two methods described above respectively measure pressure at the surface of the skin and blood volume, and this information may be more useful when synchronized with information regarding the patient's pulse. However, a combined sensor, including two sensors respectively used in the two methods, may be complicated to use because a location at which the pressure at the surface of the skin is to be detected may differ from a location at which the blood volume-change is to be detected. Also, miniaturization of such a sensor for simultaneously detecting the body surface pressure and the blood volume may also be difficult.

SUMMARY

One or more exemplary embodiments may provide an apparatus for simultaneously detecting a skin surface pressure and a blood volume by using an optical device and a method of detecting the same.

Additional exemplary aspects will be set forth in part in the description which follows and, in part, will be apparent from the description, or may be learned by practice of the presented exemplary embodiments.

According to an aspect of an exemplary embodiment, an apparatus for simultaneously detecting surface pressure and blood volume of an object may include: a printed circuit board (PCB); a light emitter disposed on the PCB and configured to emit light of a first wavelength and light of a second wavelength; a first light receiver and a second light receiver disposed on the PCB, the first light receiver configured to detect the light of the first wavelength and the second light receiver configured to detect light of the second wavelength; a transparent elastic body on the PCB and covering the light emitter, the first light receiver, and the second light receiver; and a dichroic coating disposed on the transparent elastic body and configured to reflect the light of the first wavelength and to transmit the light of the second wavelength.

The first wavelength may be shorter than the second wavelength.

The light of the first wavelength may be green light and the light of the second wavelength light may be orange light.

The light emitter may be a laser diode.

The transparent elastic body may be formed of silicon or a styrenic block copolymer.

The transparent elastic body may have a thickness in a range of about 2 mm to about 10 mm.

The dichroic coating may be a metal coating.

The dichroic coating may be formed of aluminum.

The first light receiver may include a first color filter formed thereon and the first color filter selectively transmits light of the first wavelength; and the second light-receiving unit may include a second color filter formed therein and the second color filter selectively transmits light of the second wavelength light.

According to an aspect of another exemplary embodiment, the light emitter may include a first light emitter that emits light of the first wavelength light and a second light emitter that emits light of the second wavelength light.

According to an aspect of another exemplary embodiment, the first light receiver and the second light receiver may be a single light receiver which detects both light of the first wavelength and light of the second wavelength; the first and second light emitters may alternately emit light of the first wavelength and light of the second wavelength; and the single light receiver may generate electrical signals distinguishable from each other in response to alternately receiving light of the first wavelength and light of the second wavelength.

The apparatus may be wearable on the object.

According to an aspect of another exemplary embodiment, a method of simultaneously detecting surface pressure and blood volume of an object by using the apparatus described above, the method includes: positioning the apparatus such that the dichroic coating is in contact with a skin of the object in order to transmit a curvature of the skin that occurs due to blood flow variation in a blood vessel under the skin to the dichroic coating: irradiating the skin of the object with light of the first wavelength and light of the second wavelength; calculating a surface pressure of the object by detecting light of the first wavelength that is reflected by the dichroic coating; and calculating blood volume by detecting light of the second wavelength that is returned back to the apparatus after passing through the dichroic coating and being scattered in the skin and passing through the dichroic coating toward the apparatus.

The calculating of the body-surface pressure may include measuring the curvature of the skin of the object by measuring an optical path of light of the first wavelength to the skin based on an intensity of the detected light of the first wavelength.

The calculating of the blood volume may include calculating a change in the blood volume based on a change in an intensity of the detected light of the second wavelength.

BRIEF DESCRIPTION OF THE DRAWINGS

These and/or other exemplary aspects and advantages will become apparent and more readily appreciated from the following description of exemplary embodiments, taken in conjunction with the accompanying drawings in which.

DETAILED DESCRIPTION

Reference will now be made in detail to exemplary embodiments which are illustrated in the accompanying drawings. In the drawings, the thicknesses of layers and regions are exaggerated for clarity. The embodiments described below are merely exemplary, and thus, may be embodied in many different forms.

It will be understood that when an element or layer is referred to as being "above" or "on" another element or layer, the element or layer may be directly on another element or layer or intervening elements or layers.

It will be understood that, although the terms "first", "second", etc. may be used herein to describe various elements, these elements should not be limited by these terms. These terms are only used to distinguish one element from another element.

The singular forms include the plural forms unless the context clearly indicates otherwise. It will be understood that when a part "comprise(s)" a constituent element, the constituent element is not excluded but may further include the constituent element unless there is a specifically contradict element.

Also, the terminology " . . . unit" or "module" used in the specification denotes a unit that processes at least one function or operation, and the unit may be realized as hardware or software, or a combination of hardware and software.

Figure 1:
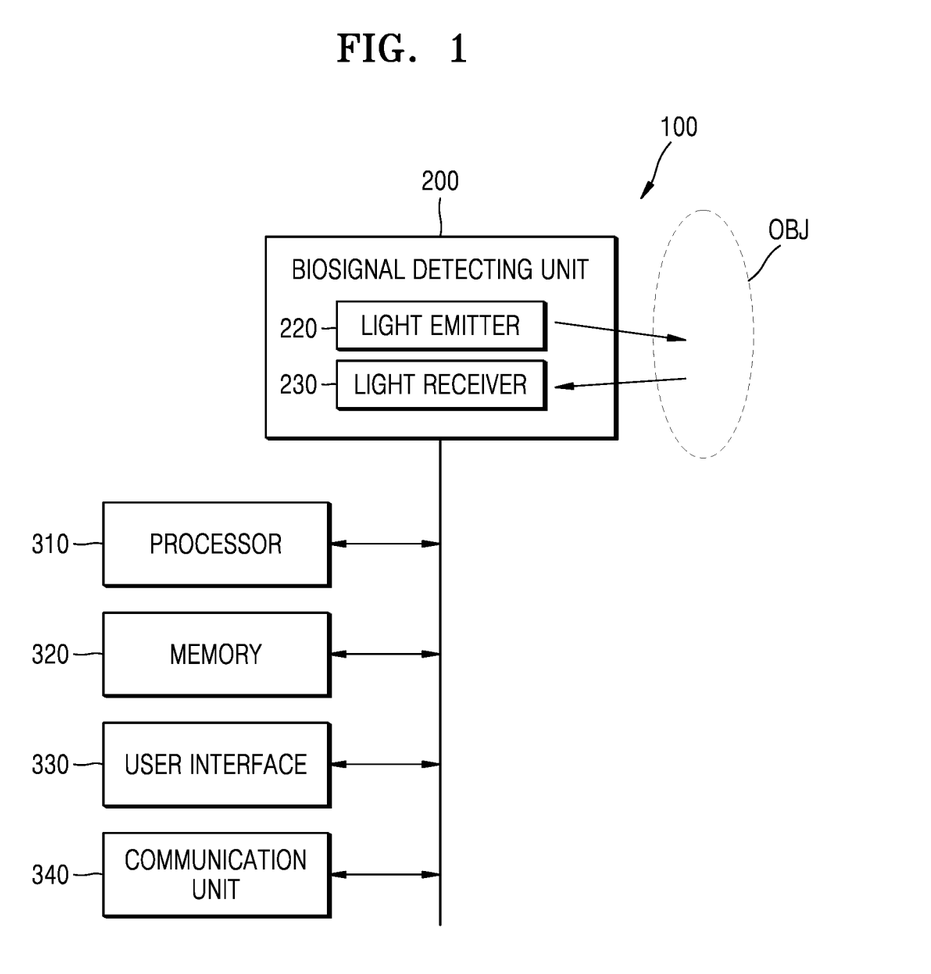
FIG. 1 is a schematic block diagram showing a configuration of an apparatus for simultaneously detecting a surface pressure and a blood volume of an object, according to an exemplary embodiment.

FIG. 1 is a schematic block diagram showing a configuration of an apparatus 100 for simultaneously detecting a surface pressure and a blood volume of an object, according to an exemplary embodiment.

Referring to FIG. 1, the apparatus 100 for simultaneously detecting a surface pressure and a blood volume of an object includes a biosignal detecting unit 200 and a processor 310 that controls the biosignal detecting unit 200 and performs various processes for analyzing bio-information based on the detected result. The apparatus 100 for simultaneously detecting a surface pressure and a blood volume of an object may further include a memory 320 and a user interface 330.

The biosignal detecting unit 200 includes a light emitter 220 and a light receiver 230. The light emitter 220 irradiates an object OBJ with light, and the light receiver 230 detects light scattered by and reflected from the object OBJ. The detected optical signal is used in various ways for analyzing bio information, which will be described below.

The object OBJ may be a biological element, for example a body part of a patient through which a pulse wave measurement is possible using photoplethysmography (PPG), that may contact or be located adjacent to the biosignal detecting unit 200 of the apparatus 100. For example, the body part of the patient may be a surface of a patient's wrist adjacent to a radial artery. When a pulse wave is detected at the skin surface of the patient's wrist through which the radial artery passes, the effect of external factors, such as the thickness of the skin of the inner wrist, that may cause detection errors, may be lessened. The radial artery is a blood vessel that is located in a position of a patient's body enabling blood pressure to be measured more accurately from the radial artery than from other blood vessels in the wrist. However, the object OBJ is not limited thereto, and may be any of a number of other peripheral body parts of a patient in which a blood vessel density is high, such as a patient's fingers, toes, or ear lobes.

The apparatus 100 may be a wearable device that may be worn on the object under examination OBJ. For example, the apparatus 100 may be a wrist watch type, a bracelet type, a wrist band type, or a hair band type, but is not limited thereto.

Alternately, rather than the whole apparatus 100, a portion of the apparatus 100, for example, the biosignal detecting unit 200, may be configured as a wearable device to be worn on the object OBJ.

Figure 2:
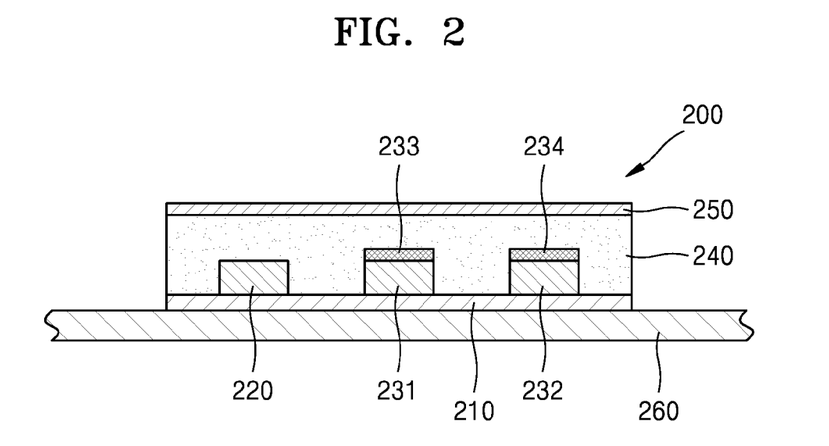
FIG. 2 is a schematic cross-sectional view of a biosignal detecting unit of an apparatus for simultaneously detecting a surface pressure and a blood volume of an object, according to an exemplary embodiment.

FIG. 2 is a schematic cross-sectional view of the biosignal detecting unit 200 of the apparatus 100, according to an exemplary embodiment.

Referring to FIG. 2, the biosignal detecting unit 200 of the apparatus 100 includes a light emitter 220, a first light receiver 231, and a second light receiver 232, that are disposed on a printed circuit board (PCB) 210, and a transparent elastic body 240 that covers the light emitter 220, the first light receiver 231, and the second light receiver 232 on the PCB 210. The first light receiver 231 and the second light receiver 232 correspond to the light receiver 230 of FIG. 1. A dichroic coating 250 may be formed on the transparent elastic body 240. The PCB 210 may be mounted on a pressing band 260. The pressing band 260 may apply a predetermined amount of pressure to the transparent elastic body 240 so that the transparent elastic body 240 tightly contacts a skin of the object OBJ. The pressing band 260 may be a cuff.

The PCB 210 may be a flexible substrate. The PCB 210 supplies power to the light emitter 220, the first light receiver 231, and the second light receiver 232 and transmits an electrical signal to the processor 310 (refer to FIG. 1) after receiving the electrical signal from the first light receiver 231 and the second light receiver 232. The processor 310 calculates the surface pressure and the blood volume of an object based on the received electrical signal.

The light emitter 220 may emit light of a first wavelength and light of a second wavelength. The first wavelength may be shorter than the second wavelength. For example, the light of the first wavelength may be green light, and the light of the second wavelength may be orange light. However, exemplary embodiments are limited thereto, and the light of the first wavelength may be red light and the light of the second wavelength may be infrared light. The light emitter 220 may be formed of a laser diode or a light-emitting device.

The first light receiver 231 detects the light of the first wavelength. The first light receiver 231 may be a photodiode, a photo transistor, or a charge-couple device (CCD). A first color filter 233 may be disposed on the first light receiver 231 to selectively transmit the light of the first wavelength.

The second light receiver 232 detects the light of the second wavelength. The second light receiver 232 may be a photodiode, a photo transistor, or a charge-couple device (CCD). A second color filter 234 may be disposed on the second light receiver 232 to selectively transmit the light of the second wavelength.

The transparent elastic body 240 may be formed of a material that tightly contacts a patient's skin under which a blood vessel passes. When a predetermined pressure is applied to the transparent elastic body 240 by the pressure of a blood vessel under the patient's skin, a curvature of the surface of the transparent elastic body 240 changes according to the pressure in the blood vessel. For example, the transparent elastic body 240 may be formed of silicon or a styrenic block copolymer. Alternately, the transparent elastic body 240 may be formed of a thermoplastic elastomer.

The transparent elastic body 240 may be formed to be thin so that the surface of the transparent elastic body 240 moves in accordance with even very small movements of the skin surface of the object OBJ.

The dichroic coating 250 may be formed of a material that reflects light of the first wavelength and transmits light of the second wavelength. The dichroic coating 250 may be a metal coating, for example, an aluminum coating. The dichroic coating 250 may be formed to a thickness in a range from about 10 μm to about 500 μm. However, the dichroic coating 250 according to exemplary embodiments is not limited thereto. The dichroic coating 250 may be a metal, such as silver or gold, a dielectric material, such as magnesium fluoride, silicon dioxide, tantalum pentoxide, zinc sulfide, or titanium dioxide, or a combination of these materials. Alternately, the dichroic coating 250 may be formed as multiple layers of these materials.

The dichroic coating 250 may be formed using a physical vapor deposition method such as sputtering, evaporative deposition, and ion beam deposition, a chemical vapor deposition method, and molecular beam epitaxy method.

Referring to FIG. 1, a program for processing and controlling the processor 310 may be stored in the memory 320, and data that is inputted thereto and outputted therefrom may be stored. For example, a program for analyzing bio-information performed in the processor 310 may be stored as code. Also, detection results that are detected by the biosignal detecting unit 200 and are required for processing in the processor 310 may be stored in the memory 320.

The memory 320 may include at least one type of storage medium, for example, a flash memory, a hard disk, a multimedia card micro, a card memory (for example, secure digital (SD) or extreme digital (XD) memory etc.), a random access memory (RAM), a static random access memory (SRAM), a read-only memory (ROM), an electrically erasable programmable read-only memory (EEPROM), a programmable read-only memory (PROM), a magnetic memory, a magnetic disc, an optical disc, or another type of memory as would be understood by one of skill in the art.

The user interface 330 is an interface between the apparatus 100 and the user and/or an external device, and includes an input unit and an output unit. The user may be an object OBJ, bio information of which is to be detected, and also may be a person or a specialist who uses the apparatus 100, that is, the term "user" is intended to be broader than the object OBJ. Information required for operating the apparatus 100 is inputted thereto and analyzed results are outputted therefrom through the user interface 330. The user interface 330 may include, for example, a button, a connector, or a display unit, and also, may further include a device, such as an acoustic output unit and a vibrating motor.

The apparatus 100 may further include a communication unit 340 for transmitting analyzed results to an external device. The external device may be medical equipment that uses the analyzed bio information, a printer for printing the analyzed result, or a display device for displaying the analyzed result. Additionally, the external device may be a smart phone, a mobile phone, a personal digital assistant (PDA), a laptop, a personal computer (PC), and mobile or non-mobile computer equipment, but the exemplary embodiments are not limited thereto.

The communication unit 340 may be connected to an external device via a wireless method or wires. The communication unit 340 may communicate with the external devices via, for example, a bluetooth communication unit, a bluetooth low energy (BLE) communication unit, a near field communication unit, a WLAN (wifi) communication unit, a zigbee communication unit, an infrared Data Association (IrDA) communication unit, a WFD (Wi-Fi Direct) communication unit, an ultra wideband (UWB) communication unit, or another device as would be understood by one of skill in the art.

Using the apparatus 100, for simultaneously detecting surface pressure and blood volume of an object, since the surface pressure and blood volume of an object may be detected at the same position on the skin of the object OBJ, an additional characteristic of the patient's cardiovascular system may be detected. For example, the blood pressure and the elasticity of the blood vessel may both be accurately detected by detecting a pulse wave at the patient's wrist using the apparatus 100.

Hereinafter, a method of simultaneously detecting a surface pressure and a blood volume of an object will be described with reference to FIGS. 3 and 4.

Figure 3:
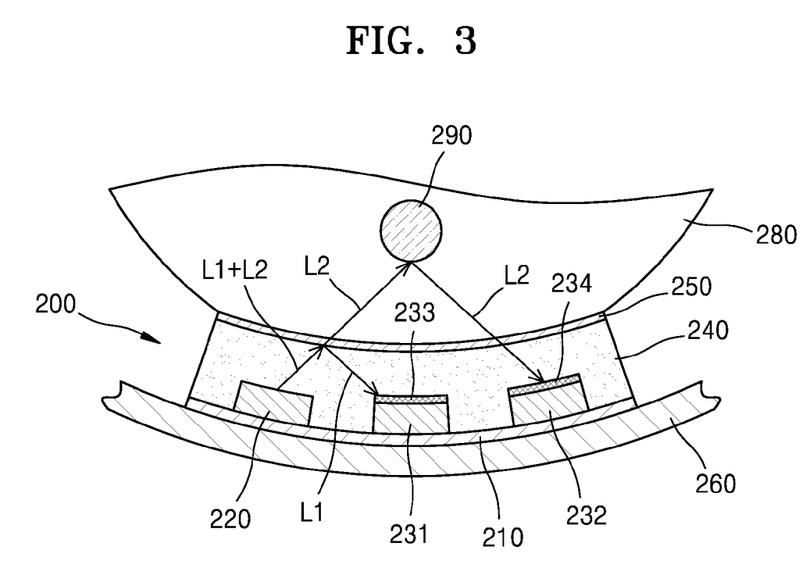
FIG. 3 is a schematic cross-sectional view for explaining a method of simultaneously detecting a surface pressure and a blood volume of an object, according to an exemplary embodiment.

FIG. 3 is a schematic cross-sectional view for explaining a method of simultaneously detecting surface pressure and blood volume of an object, according to an exemplary embodiment. FIG. 4 is a flow diagram of a method of simultaneously detecting surface pressure and blood volume of an object, according to an exemplary embodiment.

Figure 4:
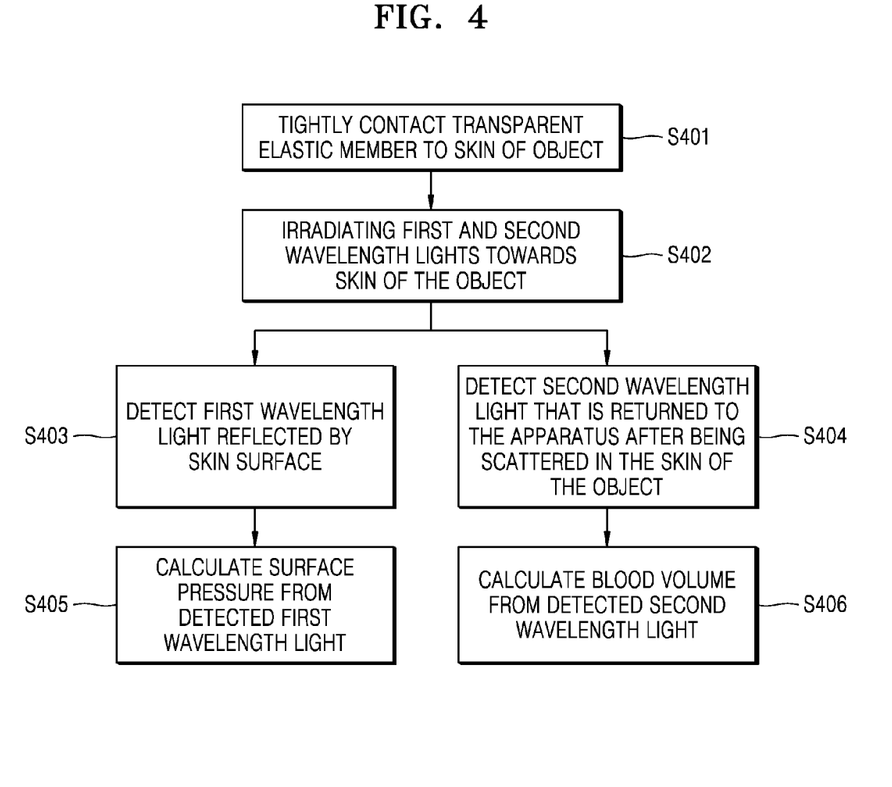
FIG. 4 is a flow diagram of a method of simultaneously detecting a surface pressure and a blood volume of an object, according to an exemplary embodiment.

Referring to FIGS. 3 and 4, the transparent elastic body 240 of the biosignal detecting unit 200 is positioned to tightly contact an object 280 (S401). Thus, the dichroic coating 250 is in contact with the skin of the object 280. At this point, a predetermined pressure is applied to the transparent elastic body 240 so that the surface curvature of the skin of the object 280 is transmitted to the transparent elastic body 240. For example, the transparent elastic body 240 is tightly contacted with the skin of the object 280 by using the pressing band 260.

Next, light is irradiated onto a blood vessel, for example a radial artery 290 in the skin of the object 280, from the light emitter 220 (S402). The emitted light may have a wide range of wavelengths. For example, the emitted light may include green light and orange light. In this example, the green light is the light of the first wavelength L1 and the orange light is the light of the second wavelength L2. The light of the first wavelength L1 is reflected at the dichroic coating 250 and is detected by the first light receiver 231 (S403), and the light of the second wavelength L2 is transmitted through the dichroic coating 250. A portion of the light of the second wavelength L2 is absorbed by blood in a blood vessel in the skin of the object 280, and another portion of the light of the second wavelength L2 is reflected and is detected by the second light receiver 232 after passing through the dichroic coating 250 (S404).

A surface pressure is calculated from the detected light of the first wavelength L1 (S405). The light of the first wavelength L1 that is reflected at the dichroic coating 250 is inputted into the first light receiver 231. The light reflected towards the first light receiver 231 may include light having a wide range of wavelengths. Of the reflected light, the light of the first wavelength L1 enters into the first light receiver 231 after passing through the first color filter 233 formed on an upper surface of the first light receiver 231. The first light receiver 231 generates an electrical signal in response to the quantity of the detected light of the first wavelength L1 and transmits the electrical signal to the processor 310 (refer to FIG. 1).

When the light of the first wavelength L1 is irradiated onto a region of skin which is convex due to a blood flow in the blood vessel therebelow, the light of the first wavelength L1 is reflected at the dichroic coating 250 on the convex region of skin, and thus, the optical path of the light of the first wavelength received by the first light receiver 231 is shorter than an instance in which the light of the first wavelength L1 is reflected from a planar region of skin. The light of the first wavelength L1, having a relatively shorter optical path has a relatively higher optical intensity, and the light of the first wavelength L1 having a relatively longer optical path has a relatively lower optical intensity. Thus, the height of the convex region of the skin may be determined from the intensity of the received light of the first wavelength L1. Also, when a frequency of the appearance of the convex region is detected, a number of pulses may be determined. Accordingly, a surface pressure may be obtained from the light of the first wavelength L1.

A blood volume is calculated from the detected light of the second wavelength L2 (S406). The light of the second wavelength L2 emitted from the light emitter 220 enters into the skin through the dichroic coating 250. The light of the second wavelength L2 incident on the skin is scattered by the skin, and some of the light of the second wavelength L2 is absorbed by blood components and a remaining portion of the light of the second wavelength light L2 is reflected to the second light receiver 232. Of the reflected light of the second wavelength L2, only light which is the same color as that of the second color filter 234 is incident onto the second light receiver 232. The second light receiver 232 generates an electrical signal in response to the detected light of the second wavelength L2 and transmits the electrical signal to the processor 310. The processor 310 calculates a blood volume from the received light of the second wavelength L2.

According to this exemplary method of simultaneously detecting surface pressure and blood volume of an object, the surface pressure and blood volume of an object may be simultaneously detected by emitting light toward the same position of a skin by using the same light emitter 220.

Figure 5:
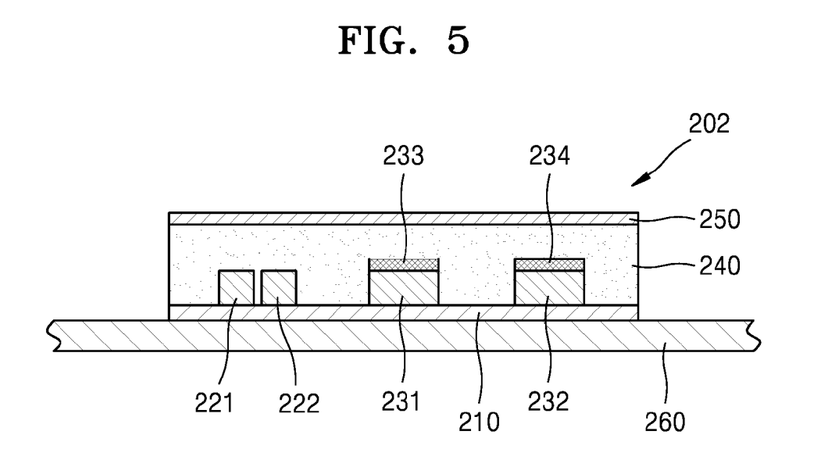
FIG. 5 is a schematic cross-sectional view of a biosignal detecting unit of an apparatus for simultaneously detecting a surface pressure and a blood volume of an object, according to an exemplary embodiment.

FIG. 5 is a schematic cross-sectional view of a biosignal detecting unit 202 of an apparatus 100 for simultaneously detecting surface pressure and blood volume of an object, according to an exemplary embodiment. Like reference numerals are used to indicate elements that are substantially identical to the elements of FIG. 2, and thus the detailed description thereof will not be repeated.

Referring to FIG. 5, the biosignal detecting unit 202 of the apparatus 100 includes a first light emitter 221 that emits light of a first wavelength, a second light emitter 222 that emits light of a second wavelength, a first light receiver 231 that detects the light of the first wavelength, and a second light receiver 232 that detects the light of the second wavelength. The first light emitter 221, the second light emitter 222, the first light receiver 231, and the second light receiver 232 are disposed on a PCB 210. A transparent elastic body 240 is formed on the PCB 210 to cover the first light emitter 221, the second light emitter 222, the first light receiver 231, and the second light receiver 232. A dichroic coating 250 facing the PCB 210 is formed on the transparent elastic body 240. The first and second light emitters 221 and 222 correspond to the light emitter 220 of FIG. 1.

The PCB 210 may be a flexible substrate. The PCB 210 supplies power to the first light emitter 221, the second light emitter 222, the first light receiver 231, and the second light receiver 232 and transmits electrical signals to the processor 310 (refer to FIG. 1) after receiving the electrical signals from the first light receiver 231 and the second light receiver 232. The processor 310 calculates a surface pressure and a blood volume of an object based on the received electrical signal.

The first wavelength may be shorter than the second wavelength. For example, the first wavelength may be green light, and the second wavelength may be orange light. The first light emitter 221 and the second light emitter 222 may each be a laser diode or a light-emitting device.

The biosignal detecting unit 202 of the apparatus 100, according to an exemplary embodiment, includes light emitters that separately emit the light of the first wavelength and the light of the second wavelength, and thus, the light emitted from the light emitters may be easily controlled.

The operation of the apparatus 100 may be readily understood from the exemplary embodiments described above, and thus, the description thereof will not be repeated.

Figure 6:
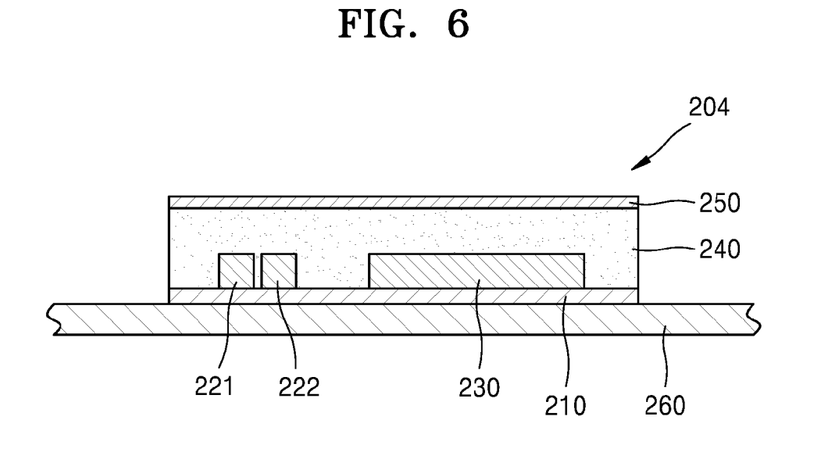
FIG. 6 is a schematic cross-sectional view of a biosignal detecting unit of an apparatus for simultaneously detecting a surface pressure and a blood volume of an object, according to an exemplary embodiment.

FIG. 6 is a schematic cross-sectional view of a biosignal detecting unit 204 of an apparatus 100 for simultaneously detecting surface pressure and blood volume of an object, according to an exemplary embodiment. Like reference numerals are used to indicate elements that are substantially identical to the elements of FIG. 2, and thus the detailed description thereof will not be repeated.

Referring to FIG. 6, the biosignal detecting unit 204 of the apparatus 100 includes a first light emitter 221 that emits light of a first wavelength, a second light emitter 222 that emits light of a second wavelength, and a light receiver 230 that detects the light of the first wavelength and the light of the second wavelength. The first light emitter 221, the second light emitter 222, and the light receiver 230 are disposed on a PCB 210. A transparent elastic body 240 is formed on the PCB 210 to cover the first light emitter 221, the second light emitter 222, and the light receiver 230. A dichroic coating 250 facing the PCB 210 is formed on the transparent elastic body 240.

The first light emitter 221 and the second light emitter 222 may alternately emit the light of the first wavelength and the light of the second wavelength, as controlled by the processor 310. The light receiver 230 may receive the light of the first wavelength and the light of the second wavelength at given predetermined times. The light receiver 230 generates a first electrical signal in response to the intensity of the light of the first wavelength and a second electrical signal in response to the intensity of the light of the second wavelength, and transmits the first electrical signal and the second electrical signal to the processor 310.

The operation of the apparatus 100 for simultaneously detecting surface pressure and blood volume of an object may be readily understood from the exemplary embodiments described above, and thus, the description thereof will not be repeated.

The biosignal detecting unit 204 of the apparatus 100, according to an exemplary embodiment includes light emitters that distinctively emit light of a first wavelength and light of a second wavelength and a single light receiver that alternatively receives the light of the first wavelength and the light of the second wavelength, and thus, a color filter is unnecessary on the light receiver.

According to one or more of the above-described exemplary embodiments, the apparatus for simultaneously detecting surface pressure and blood volume of an object may detect a surface pressure and a blood volume of an object at the same position on the skin of an object, and thus, an additional accurate characteristic of a patient's cardiovascular system may be detected.

Also, an exemplary apparatus for simultaneously detecting surface pressure and blood volume of an object is configured of a single optical sensor without using an additional pressure measuring device, and thus, the apparatus may be miniaturized and used on a wearable device.

While one or more exemplary embodiments have been described with reference to the figures, it will be understood by those of ordinary skill in the art that various changes in form and details may be made therein without departing from the spirit and scope as defined by the following claims.

What is claimed is:

1. A detecting apparatus comprising:
   a light emitter configured to emit light of a first wavelength and light of a second wavelength, different from the first wavelength;
   a detector configured to detect light of the first wavelength and light of the second wavelength;
   a transparent elastic body covering the light emitter, and the detector; and
   a dichroic coating disposed on the transparent elastic body, wherein the dichroic coating reflects light of the first wavelength emitted from the light emitter and transmits light of the second wavelength emitted from the light emitter.

2. The apparatus of claim 1, further comprising a printed circuit board (PCB),
   wherein the light emitter is disposed on the PCB, and
   the detector comprises a first light receiver disposed on the PCB, the first light receiver configured to detect light of the first wavelength, and a second light receiver disposed on the PCB, the second light receiver configured to detect light of the second wavelength.

3. The apparatus of claim 2, wherein
   the first light receiver comprises a first color filter disposed thereon, wherein the first color filter selectively transmits light of the first wavelength, and
   the second light receiver comprises a second color filter disposed thereon, wherein the second color filter selectively transmits light of the second wavelength.

4. The apparatus of claim 2, wherein the light emitter comprises a first light emitter configured to emit light of the first wavelength and a second light emitter configured to emit light of the second wavelength.

5. The apparatus of claim 4, wherein
   the first light receiver and the second light receiver are a single light receiver configured to detect both light of the first wavelength and light of the second wavelength;
   the first light emitter and the second light emitter are configured to alternately emit light of the first wavelength and light of the second wavelength; and
   the single light receiver is configured to generate a first electrical signal in response to receiving the light of the first wavelength and is configured to generate a second electrical signal, distinguishable from the first electrical signal, in response to receiving light of the second wavelength.

6. The apparatus of claim 1, wherein the first wavelength is shorter than the second wavelength.

7. The apparatus of claim 6, wherein the light of the first wavelength is green light and the light of the second wavelength is orange light.

8. The apparatus of claim 1, wherein the light emitter is a laser diode.

9. The apparatus of claim 1, wherein the transparent elastic body comprises one of silicon and a styrenic block copolymer.

10. The apparatus of claim 9, wherein the transparent elastic body has a thickness in a range of about 2 mm to about 10 mm.

11. The apparatus of claim 9, wherein the dichroic coating comprises metal.

12. The apparatus of claim 11, wherein the dichroic coating comprises aluminum.

13. The apparatus of claim 1, wherein the object is a body part of a patient and the apparatus is configured to be wearable on the body part of the patient.

* * * * *